United States Patent [19]

Dessauer et al.

[11] Patent Number: 5,320,945
[45] Date of Patent: Jun. 14, 1994

[54] METHOD AND REAGENT FOR THE DETERMINATION OF ANTITHROMBIN III

[75] Inventors: Andreas Dessauer, Tutzing; Reinhard Herz, Pöcking-Possenhofen; Helmut Lill, Wielenbach, all of Fed. Rep. of Germany

[73] Assignee: Boehringer Mannheim GmbH, Mannheim-Waldorf, Fed. Rep. of Germany

[21] Appl. No.: 122,133

[22] Filed: Sep. 15, 1993

Related U.S. Application Data

[63] Continuation of Ser. No. 886,295, May 21, 1992, abandoned, which is a continuation of Ser. No. 551,544, Jul. 11, 1990, abandoned.

[30] Foreign Application Priority Data

Jul. 14, 1989 [DE] Fed. Rep. of Germany ....... 3923340

[51] Int. Cl.$^5$ .............................................. C12Q 1/56
[52] U.S. Cl. .......................................... 435/13; 436/69
[58] Field of Search ............................. 435/13; 436/69

[56] References Cited

U.S. PATENT DOCUMENTS

| 4,409,327 | 10/1983 | Bartl et al. | 435/13 |
|---|---|---|---|
| 4,473,639 | 9/1984 | Sommer et al. | 435/13 |
| 4,480,030 | 10/1984 | Svendsen | 436/69 |
| 4,508,644 | 4/1985 | Heber et al. | |
| 4,543,335 | 9/1985 | Sommer et al. | 436/69 |
| 4,665,016 | 5/1987 | Heber et al. | 435/23 |
| 4,683,291 | 7/1987 | Zimmerman et al. | 530/324 |
| 4,740,588 | 4/1988 | Adams et al. | 530/328 |
| 4,748,116 | 5/1988 | Simonsson et al. | 435/23 |
| 4,748,156 | 5/1988 | Aoki et al. | 530/350 |
| 4,957,903 | 9/1990 | Ranby | 435/13 |

FOREIGN PATENT DOCUMENTS

| 0034320 | 8/1981 | European Pat. Off. | |
| 0103247 | 3/1984 | European Pat. Off. | |
| 0110306 | 6/1984 | European Pat. Off. | |
| 3734889 | 4/1988 | Fed. Rep. of Germany | 436/69 |
| 1193587 | 11/1985 | U.S.S.R. | 436/69 |
| 1464090 | 3/1989 | U.S.S.R. | 436/69 |

OTHER PUBLICATIONS

Miraglia et al., Anal. Biochem., 144, pp. 165–171 (1985).
H. Lill, et al. (1984) "Methods of Enzymatic Analysis", vol. 5 3rd Edition, pp. 441–448.
Analytical Biochemistry (1985) vol. 144, pp. 165–171.

*Primary Examiner*—Jill A. Johnston
*Attorney, Agent, or Firm*—Felfe & Lynch

[57] ABSTRACT

In order to determine antithrombin III in body fluids by reacting the sample with thrombin and a chromogenic substrate which forms a colour by the action of thrombin and measurement of the colour formed, the reaction is carried out in the presence of denaturing agents or of the tetrapeptide Gly-Pro-Arg-Pro and an oligopeptide is used as the substrate which has a sensitivity to thrombin which is a factor of 5 to 100-fold lower compared With Tos-Gly-Pro-Arg-pNA

8 Claims, No Drawings

METHOD AND REAGENT FOR THE DETERMINATION OF ANTITHROMBIN III

This application is a continuation of application Ser. No. 07/886,295 filed May 21, 1992, now abandoned; which is a continuation of Ser. No. 07/551,544 filed Jul. 11, 1990, now abandoned.

DESCRIPTION

The invention concerns a method for the determination of antithrombin III in body fluids by reacting the sample with thrombin and a chromogenic substrate which forms a colour by the action of thrombin and measurement of the colour formed as well as a reagent which is suitable for this.

Antithrombin III is a factor of the blood coagulation system which has a regulatory role. Blood coagulation is initiated by different proteases interacting in a cascade. The last of the sequential activation steps liberates thrombin which in turn produces fibrin monomers by the cleavage of fibrinogen which agglomerate and form a thrombus. The most important regulator is antithrombin III (AT III) which can form a complex with thrombin and also with other proteases involved in blood coagulation which blocks the active center. The amount of antithrombin III in the blood of healthy people is in a relatively narrow range. Reduced amounts of antithrombin III may be caused by a consumptive coagulopathy, a severe liver disease or it may be hereditary. A reduced antithrombin III level is nowadays generally judged to be a thrombosis risk. Therefore, the antithrombin III level is reduced in some cases in an acute thrombosis. The amount of antithrombin III is thus a valuable parameter in clinical diagnosis.

Different procedures are already known for the detection of antithrombin III which are based on immunological methods and also on the use of chromogenic substrates. In the latter case, thrombin is added to the sample which reacts with the antithrombin III present in the sample and is inactivated. Excess thrombin is detected by incubation with a chromogenic substrate which forms a coloured substance by the action of thrombin and measurement of the colour formed, wherein the amount of antithrombin III is inversely proportional to the colour formed. Methods for the determination of antithrombin III are described for example in Bergmeyer, "Methods of Enzymatic Analysis", 3rd edition, Verlag Chemie, Vol. 5, p. 441–448; I. Witt, ed., "Neue Methoden der Gerinnungsanalyse mit chromogenen Substraten", Stormorken, Neue Methoden der Gerinnungsanalyse, pages 119–121; Odegard et al., Haemostasis 7: 202–209 (1978); Fareed et al., in Chromogenic Peptide Substrates (eds. M. F. Scully and V. V. Kakkar) Churchill Livingstone (1979) 183–191 and Abildgaard et al., Thromb. Res. 11, 549–553 (1977).

As a rule the samples are very highly diluted to avoid interferences in the test, since sample colour, turbidity and differences in the pH, as well as salt content of the sample have less influence on the measured result the more the amount of sample can be limited in the test solution. Thus, when carrying out kinetic determinations, in particular on automated analyzers, sample dilutions ranging up to 1:1500 are used. This is, however, impractical for the routine (especially the emergency situation).

It was therefore the object of the invention to improve the known detection methods and to provide a method which can be carried out on automated analyzers, in a short time and without sample dilution and which enables the use of a single standard.

This object is achieved by a method for the determination of antithrombin III in body fluids by reacting the sample with thrombin and a chromogenic substrate which forms a colour by the action of thrombin, and measurement of the colour formed, which is characterized in that the reaction is carried out in the presence of denaturing agents or of the tetrapeptide Gly-Pro-Arg-Pro and in which an oligopeptide substrate is used as the substrate which has a sensitivity to thrombin which is a factor of 5 to 100 lower compared with Tos-Gly-Pro-Arg-pNA.

Surprisingly, it was possible to determine antithrombin III exactly and reproducibly by the addition of denaturing agents or a tetrapeptide and by use of a relatively insensitive oligopeptide substrate for thrombin, whereby long test runs can be performed without restrictions on automated analyzers.

In order to determine antithrombin III in a body fluid, a sample solution is mixed with thrombin in excess (with respect to antithrombin III). In this process, complexes are formed from antithrombin III and thrombin. Thrombin complexed in this way no longer has any protease activity. A substrate is added to the solution which is cleaved by thrombin and thereby forms a colour. Only the thrombin which is in excess and is not complexed reacts with the substrate. The measured signal is inversely proportional to the antithrombin III concentration of the sample. Heparin, which accelerates the reaction between antithrombin III and thrombin, is preferably added to carry out the method.

There are a multitude of substrates which are suitable for this method of which Tos-Gly-Pro-Arg-pNA-acetate (Chromozym® TH) is used most often. This reagent is highly sensitive.

According to the present invention, a denaturing agent or the tetrapeptide Gly-Pro-Arg-Pro is added in addition in the first step. It was found that the initial thrombin value did not remain constant in long test series when using undiluted samples. This is rectified by addition of the components mentioned above. Substances are suitable as denaturing agents which are known in this field. Urea or guanidinium hydrochloride are preferably used. The denaturing agent is preferably used in a concentration of 0.1 to 1 mol/l in the test or 1 to 6 mol/l in the substrate solution. If the tetrapeptide is used as the component, this is then added in a concentration in the range between 0.04 to 1 mg/ml in the test.

The denaturing agent or the tetrapeptide can either already be added to the reagent solution or they can also be added when the sample solution is incubated with the reagent solution. If urea is used as the denaturing agent then it is advantageous to first add the urea together with the substrate, since urea has an unfavourable influence on the stability of thrombin.

A further key feature of the method according to the present invention is the use of a chromogenic oligopeptide substrate for thrombin whose sensitivity, however, is a factor 5 to 100 lower compared with Chromozym®TH. All substrates which fulfill this criterium are suitable such as e.g.

CBZ-Val-Gly-Arg-pNA;
H-D-Pro-Phe-Arg-pNA;
H-D-Val-Leu-Arg-pNA;
Bz-Val-Leu-Arg-pNA;
Bz-Leu-Leu-Arg-pNA;

Bz-Phe-Leu-Arg-pNA as well as
Bz-Leu-Ile-Arg-pNA.

CBZ: carbobenzoxy, Bz: benzoyl, D-Pro: D-proline, D-Val: D-valine, pNA: p-nitroaniline).

All these exemplary compounds mentioned above have p-nitroaniline as a chromophore which is cleaved off by thrombin. Other usual chromophores are equally suitable such as e.g. 5-amino-2-nitrobenzoic acid or methoxynitroaniline, which can be present in the substrate instead of pNA. A peptide of the formula R-OCO-Gly-Pro-Arg-pNA is preferably used as the substrate in which R denotes an alkyl residue with 1 to 3 C atoms and is preferably a methyl residue.

Substrates which have a sensitivity which is reduced by a factor 10 to 30 compared to Chromozym ®TH are particularly preferably used.

The concentration of the substrate as it is present in the test solution depends on its Michaelis constant. Substrate concentrations are suitable which are in a range from 2 to 20 times the respective Michaelis constants.

The thrombin concentration used for the method can, according to the present invention, be increased up to times, preferably 7 to 15 times the thrombin concentration used according to the state of the art; this corresponds to up to 630 U thrombin/l (international enzyme units of thrombin with Tos-Gly-Pro-Arg-pNA as substrate at 25° C.) test solution. Within this range, but however, not with less thrombin, a linear calibration curve can be obtained with the method according to the present invention so that a kinetic determination can be carried out over a wide range and, above all, a convenient test procedure with only one standard on automated analyzers is possible. If it is not linear over the measurement range then several standards have to be used which hinders the rapid application of the test, which is for example essential for the emergency situation.

The amount of sample depends on the measurement range of the test and on the technical feasibility. The lower limit is 1 µl for automated analyzers. The upper limit depends on the type of analyzer and is not usually more than 5 µl. If the amount of sample is larger then, if the other test conditions remain the same, a smaller measurement range is available and, in addition, interferences by formation of fibrin occur to an increasing extent when the amount of sample is larger. On the other hand, the actual measurement signal is reduced when using smaller amounts of sample which, together with the increasing inaccuracy when pipetting very small volumes, leads to a worsening of the test precision.

A further object of the invention is a reagent for the determination of antithrombin III which contains thrombin, a denaturing agent or the tetrapeptide Gly-Pro-Arg-Pro as well as a chromogenic substrate which forms a colour by the action of thrombin and which is a factor of 5 to 100-fold less sensitive with respect to thrombin compared to Chromozym ®TH.

In a preferred embodiment the reagent also contains heparin.

The invention is elucidated by the following Examples:

EXAMPLE 1 (COMPARISON)

(Method according to the state of the art, Bergmeyer)

1 part thrombin (500 U/l) is mixed with 20 parts Tris/HCl buffer, pH 8.1 containing at the same time heparin in a sufficient amount (2 USP units/ml). To measure the initial thrombin value, 0.10 ml physiological saline solution and at the start of the enzyme/substrate reaction 0.200 ml thrombin substrate solution (Chromozym ®TH: Tos-Gly-Pro-Arg-pNA, 0.16 mmol/l in the test mixture) were added to 2 ml of this thrombin reagent. In the test mixture thus defined, reaction rates ($\Delta A$/min) were achieved at 405 nm of 0.220 at 25° C. and 0.400 at 37° C.

EXAMPLE 2

Antithrombin III was determined in sample solutions according to the method described in Example 1 in which, however, Chromozym ®TH was replaced by the substrate according to the present invention.

Manual test without sample pre-dilution:
0.01 ml undiluted sample (corresponding to 6.6 µl sample per ml test volume)
1.25 ml thrombin reagent (308 U/l thrombin in the test, 14.74-fold compared to the state of the art)
0.25 ml substrate (0.298 mmol/l methyl-OCO-Gly-Pro-Arg-pNA, 0.5 mol/l urea in the test).
Tests on automated analyzers:
Hitachi 704/705:
0.003 ml undiluted sample (corresponding to 7.1 µl sample per ml test volume)
0.350 ml thrombin reagent (308 U/l thrombin and 248 mg/l Gly-Pro-Arg-Pro in the test)
0.070 ml substrate (0.298 mmol/l MeOCO-Gly-Pro-Arg-pNA in the test.
Hitachi 717:
0.002 ml undiluted sample (corresponding to 6.6 µl sample per ml test volume)
0.250 ml thrombin reagent (308 U/l thrombin and 248 mg/l Gly-Pro-Arg-Pro in the test)
0.050 ml substrate (0.298 mmol/l MeOCO-Gly-Pro-Arg-pNA in the test)

Table 1

Comparison of the initial thrombin values (without sample) under the test conditions chosen here using Chromozym ®TH and MeOCO-Gly-Pro-Arg-pNA:

|  | MeOCO—Gly... ($\Delta A$/min) | Chromozym$^R$ TH ($\Delta A$/min) |
| --- | --- | --- |
| Hitachi 717, 37° C. | 0.400 | 5.700 |
| Hitachi 717, 25° C. | 0.200 | 2.900 |
| Hitachi 704, 37° C. | 0.300 | 4.300 |
| Hitachi 704, 25° C. | 0.150 | 2.100 |

The measurement limit of kinetic enzyme/substrate reactions is ca 1.00 $\Delta A$/min for the Hitachi instruments. The other known analyzers also run into analytical limits which are not feasible at these high values for $\Delta A$/min. The same, of course, applies to the manual test in which, under the conditions described above without sample predilution and using Chromozym ®TH as substrate, $\Delta A$-values of 3.3 at 25° C. and of 6.0 at 37° C. would occur.

TABLE II

Test instrument: Hitachi 717
Test mixture: 0.002 ml undiluted sample
0.250 ml thrombin reagent; 14.74-fold in comparison with the state of the art
(=308 U/L in the test)
0.050 ml substrate

| substrate sensitivity (% of Chromozym ® TH) | thrombin concentration in the test | | | | | |
|---|---|---|---|---|---|---|
| | 7.5-fold (156.8 U/l) | | 14.74-fold (308 U/l) | | 30-fold (627 U/l) | |
| | 25° C. | 37° C. | 25° C. | 37° C. | 25° C. | 37° C. |
| 1% | 0.014 | 0.028 | 0.029 | 0.057 | 0.058 | 0.114 |
| 2% | 0.029 | 0.057 | 0.058 | 0.114 | 0.116 | 0.228 |
| 7% | 0.100 | 0.200 | 0.200 | 0.400 | 0.400 | 0.800 |
| e.g Me—OCO—Gly—Pro—Arg-pNA 17% | 0.246 | 0.484 | 0.493 | 0.969 | 0.986 | 1.938 |
| e.g. i-Prop-OCO—Gly—Pro—Arg-pNA 20% | 0.280 | 0.560 | 0.580 | 1.140 | 1.160 | 2.280 |

It becomes clear that when using the substrates with a higher sensitivity (17% of 20% of Chromozym ®TH), not all test versions (e.g. 37° C. or higher thrombin concentrations) can be carried out with very good results; the scope within which the method according to the present invention can be carried out advantageously without sample dilutions is apparent.

We claim:

1. In a method for the determination of antithrombin III in an undiluted body fluid sample wherein the sample is reacted with excess thrombin, heparin and a chromogenic substrate which substrate forms a color with that excess of thrombin which has not reacted with antithrombin III and wherein the color formed is measured wherein the amount of antithrombin III is inversely proportional to the amount of color formed, the improvement consisting essentially of adding at least one denaturing agent or the tetrapeptide Gly-Pro-Arg-Pro to the undiluted body fluid sample, thrombin and the chromogenic substrate, and wherein the chromogenic substrate is an oligopeptide substrate which has a 5 to 100 fold lower sensitivity to thrombin as compared to the sensitivity of Tos-Gly-Pro-Arg-pNA wherein the chromogenic oligopeptide substrate is a compound selected from the group consisting of CBZ-Val-Gly-Arg-Y, H-D-Pro-Phe-Arg-Y, H-D-Val-Leu-Arg-Y, Bz-Val-Leu-Arg-Y, Bz-Leu-Leu-Arg-Y, Bz-Phe-Leu-Arg-Y, Bz-Leu-Ile-Arg-Y and a peptide of the formula R-OCO-Gly-Pro-Arg-pNA wherein R is a $C_1$–$C_3$ alkyl, and wherein Y is a chromophore selected from the group consisting of p-nitroaniline, 5-amino-nitrobenzoic acid and methoxy-nitroaniline.

2. The method of claim 1 wherein at least one denaturing agent is added and said denaturing agent is urea or guanidinium hydrochloride.

3. The method of claim 2 where the concentration of the denaturing agent is 0.1 to 1 mol/l.

4. The method of claim 1 wherein the tetrapeptide is added and the concentration of the tetrapeptide is 0.04 to 1 mg/ml.

5. The method of claim 1 wherein R is methyl.

6. A reagent for the determination of antithrombin III in an undiluted body fluid sample consisting essentially of thrombin, heparin, a denaturing agent or the tetrapeptide Gly-Pro-Arg-Pro and a chromogenic oligopeptide substrate which forms a color with excess thrombin and which has a 5 to 100 fold lower sensitivity to thrombin as compared to the sensitivity of Tos-Gly-Pro-Arg-pNA wherein the chromogenic oligopeptide substrate is a compound selected from the group consisting of CBZ-Val-Gly-Arg-Y, H-D-Pro-Phe-Arg-Y, H-D-Val-Leu-Arg-Y, Bz-Val-Gly-Arg-Y, Bz-Leu-Leu-Arg-Y, Bz-Phe-Leu-Arg-Y, Bz-Leu-Ile-Arg-Y and a peptide of the formula R-OCO-Gly-Pro-Arg-pNA wherein R is a $C_1$–$C_3$ alkyl, and Y is a chromophore selected from the group consisting of p-nitroaniline, 5-amino-nitrobenzoic acid and methoxy-nitroaniline.

7. The reagent of claim 6 wherein said reagent includes the denaturing agent and the denaturing agent is urea or guanidinium hydrochloride or the tetrapeptide Gly-Pro-Arg-Pro.

8. The reagent of claim 7 wherein R is methyl.

* * * * *